United States Patent [19]

Harjunmaa

[11] Patent Number: 4,652,136
[45] Date of Patent: Mar. 24, 1987

[54] METHOD FOR THE MEASUREMENT OF THE DIFFERENCE IN COLOR CONTENTS OF SAMPLES

[75] Inventor: Hannu Harjunmaa, Espoo, Finland

[73] Assignee: Labsystems Oy, Helsinki, Finland

[21] Appl. No.: 579,888

[22] PCT Filed: Jun. 21, 1983

[86] PCT No.: PCT/FI83/00049
§ 371 Date: Feb. 3, 1984
§ 102(e) Date: Feb. 3, 1984

[87] PCT Pub. No.: WO84/00211
PCT Pub. Date: Jan. 19, 1984

[30] Foreign Application Priority Data

Jun. 29, 1982 [FI] Finland .................................. 822305

[51] Int. Cl.$^4$ ............................................... G01J 3/51
[52] U.S. Cl. ................................... 356/408; 356/414; 356/419; 356/418; 356/425
[58] Field of Search ............... 356/402, 407, 408, 414, 356/416, 418, 419, 420, 425, 434, 445–448

[56] References Cited

U.S. PATENT DOCUMENTS

3,237,509 3/1966 Fielding ................................ 356/408
3,332,313 7/1967 Batson .................................. 356/408
3,807,873 4/1974 Nakamori ............................. 356/418

Primary Examiner—F. L. Evans

[57] ABSTRACT

Method for the measurement of the difference in the color contents of two samples (1, 2) or of two component areas of a sample, in which method one or several sources of light (3 to 6) as well as one light detector (7) are used. According to the invention, both samples (1, 2), or component areas of a sample, are illuminated simultaneously and, from both samples (1, 2) or component areas of a sample, the light is passed simultaneously to the light detector (7). The lights to be measured from the samples (1, 2) or component areas of a sample are of different colors, as compared with each other, so that the light to be measured from the first sample or component area is absorbed weakly in the coloring agent and the light to be measured from the second sample or component area is absorbed strongly in the coloring agent. The colors of the lights to be measured from the samples (1, 2) or component areas of a sample are alternated with each other at an appropriate frequency, such as, e.g., at a frequency within the range of 1 c/s to 10,000 c/s. The AC signal given by the light detector (7) is used as the measure of the difference in the color contents of the samples (1, 2) or component areas of a sample.

10 Claims, 6 Drawing Figures

ns of two samples or of two component areas of a sample, in which method one or several sources of light as well as one light detector are used.

By means of techniques known in prior art, it is possible to measure the reflectivity, transmission or absorption of one sample at one wavelength, or their difference at two wavelengths, or the difference in reflectivity, transmission or absorption of two samples at one wavelength. In the case of two samples and two wavelengths, two separate measurements are required in order that the difference could be obtained.

The method in accordance with the invention is mainly characterized in that both samples, or component areas of a sample, are illuminated simultaneously and, from both samples or component areas of a sample, the light is passed simultaneously to the light detector, the lights to be measured from the samples or component areas of a sample being of different colours, as compared with each other, so that the light to be measured from the first sample or component area is absorbed weakly in the colouring agent and the light to be measured from the second sample or component area is absorbed strongly in the colouring agent, the colours of the lights to be measured from the samples or component areas of a sample are alternated with each other at an appropriate frequency, such as, e.g., at a frequency ranging from 1 c/s to 10,000 c/s, and the AC signal given by the light detector is used as the measure of the difference in the cololur contents of the samples or component areas of a sample.

By means of the method in accordance with the invention, by means of which the difference in colour between two samples is measured at two wavelengths, the difference in colour between the samples is obtained precisely by means of one measurement.

The samples for which the method in accordance with the invention is suitable may be solid, liquid or gaseous volume samples, or faces that reflect light, or films transparent to light.

The invention comes out in more detail from the following description and from the attached drawings, wherein FIG. 6 illustrates the stabilization of the sources of light and automatic balance adjustment. In the description of the method, measurement of the difference in colour of two face samples is used as an example. The way in which the nature of the samples affects the details of the performance of the method is obvious for a person skilled in the art. Likewise, it is obvious that this method can also be applied in the ultraviolet and infrared ranges.

In the method in accordance with the invention, two lights of different colours are used, i.e. lights whose wavelength ranges are restricted in such a way that the average wavelengths of their wavelength ranges are different. The restricting of the wavelength range takes place in a way known to a person skilled in the art, such as, e.g., by means of a filter, grid, or prism. One of the face samples is called the face to be studied and the other one the reference face. Both of the faces are illuminated simultaneously, one with a light of one colour and the other with a light of the other colour, and the light reflected from both faces is allowed to act upon one light detector at the same time. The measurement geometry must be such that the angles of incidence and dispart of the light relative the face are different, i.e. that only diffusely reflected light has access to the detector. The colours of the lights are alternated with each other at an appropriate frequency, which is chosen so that both the electrical or mechanical control of the light colour and the light detector and the related electronics, such as, e.g., amplifiers, are, at the frequency concerned, capable of operating reliably and precisely. Owing to the linearity of the light detector, the information on the difference between the reflection factors is retained, and, if the faces have different colours in relation to the two wavelengths to be used, i.e. if the difference between the reflection factors of one face at these two wavelengths is different as compared with the corresponding difference regarding the other face, the light detector gives an AC signal, whose frequency is the same as the frequency of alternation of the colours and whose amplitude is in proportion to the difference in colours of the faces. The result of the measurement is independent from the darkness of the sample, i.e. from the natural component of its absorption; if one of the faces is white and the other face is black, no signal is received, because none of the faces contains a colouring agent. The result is also independent from difference in glaze of the faces. Thus, the method is in particular suitable for the measurement of differences in contents of colouring agents, once two wavelengths are found at one of which the colouring agent absorbs strongly and at the other one of which it absorbs weakly.

It is evident for a person skilled in the art that, in general, in this method, the restricting of the wavelength range of the measurement light, i.e. the selection of the colour, may also be performed after the sample, in which case the samples would be illuminated by means of white light.

Generally speaking, in the method in accordance with the invention, in order that the darkness of the sample should not affect the measurement result, it is necessary to adjust the intensity of the sources of light illuminating the same sample to such a level that they produce an equally strong signal in the light detector. The adjusting takes place in practice so that a white calibration face is placed in the place of one of the samples and a black calibration face in the place of the other sample, or, if volume samples are concerned, a non-transparent calibration sample in the place of one sample and a completely transparent, i.e. colourless, calibration sample in the place of the other sample, and the intensity of light is adjusted either electrically or by means of filters so that the AC signal of the light detector becomes zero. The places of the black and white or of the non-transparent and colourless calibration samples are reversed, and the adjustment operation is repeated. Automatic balance adjustment is accomplished by use of the apparatus in conjunction with a second light detector (25) to which samples are passed alternatingly from both beams of light (3e, 4e) of different spectral ranges at an appropriate frequency, which may be the same as or different from the frequency of alternation of spectral ranges in the measurement, and the AC signal obtained is used for adjusting the ratio of the light intensities of the sources of light (3e, 4e) so that the AC signal becomes zero, and the DC signal obtained is used for the stabilization of the light intensity of the sources of light (3e, 4e).

In addition to the possibility that the samples may be different portions of the same face, they may also be, e.g., different portions of the same liquid or gas flow.

Figure 1:
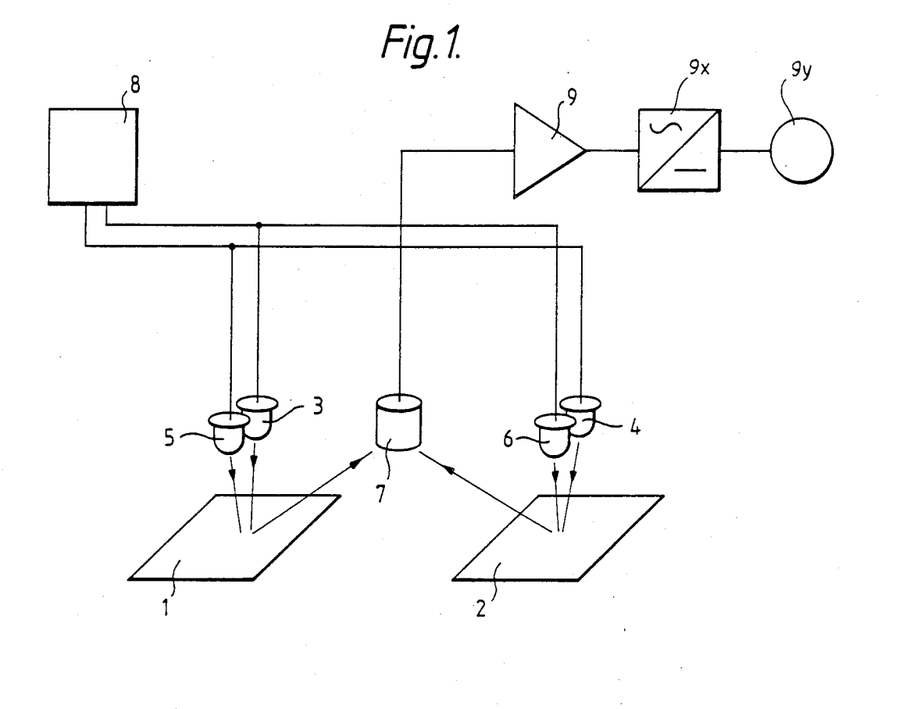
FIG. 1 illustrates the measurement process when local reddishness of the skin by the effect of increased circulation of blood is being examined.

In the example of FIG. 1, the invention is applied to local reddishness of the skin as a result of increased blood circulation. In the absorption spectrum of haemoglobin, there is a strong absorption band within the range of 500 to 600 nm, and at wavelengths longer than 600 nm there is no significant absorption. The light reflected from the skin 1, 2 is measured. As the sources of light, four light-emitting diodes (LED) 3 to 6 are used, of which two 3, 4 are green and two 5, 6 are red. The maximum wavelength of the green LED's is 565 nm and that of the red ones 635 nm. As the light detector, one phototransistor 7 is used, on which the light reflected from the two test areas 1, 2 on the skin falls.

The control unit 8 operates so that each test area 1, 2 is illuminated by one green and one red LED alternatingly so that, always when a red LED illuminates one test area, the other test area is illuminated by a green LED. The AC signal of the phototransistor is passed to the amplifier 9, rectified by rectifer 9x, and measured by meter 9y.

The reflection factors of the test areas 1, 2 in red light are denoted with $R_1$ and $R_2$ and in green light with $G_1$ and $G_2$. The range of variation of the reflection factors is 0 ... 100%. When the sources of light 3, 4 and 5, 6 alternate in the way described above, the AC signal of the light detector 7 is proportional to the equation $$S=(R_1+G_2)-(R_2+G_1)$$

which is in a simple way obtained in the form $$S=(R_1-G_1)-(R_2-G_2)$$

The following denotations are used:

$$H_1=R_1-G_1$$

$$H_2=R_2-G_2$$

From this it follows:

$$S=H_1-H_2$$

The quantities $H_1$ and $H_2$ are called H-indexes. The H-index has the nature of a colour index, and it can be used as a measure of the haemoglobin content of the skin. It receives the value 0 when the skin has no haemoglobin at all, and the value 100% when the skin is completely haemoglobin red. The measurement described above gives the difference in the H-indexes between two test areas. If, for example, the area 1 consists of normal skin, the measurement indicates the reddishness of the area 2.

It is evident for a person skilled in the art that, in the above example, the separate green and red LED's may be replaced by ones that, according to the control commands received by them, can emit either green or red light as far as their brightness is sufficient. In such a case, only two LED's would be required.

Figure 2:
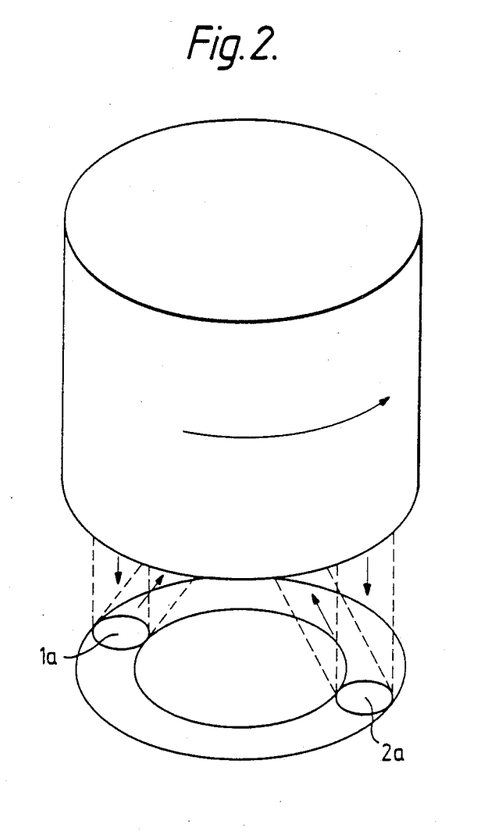
FIG. 2 illustrates the measurement of component areas of a sample when the apparatus or the optics of the apparatus are rotatad.

The alternation of the colours may, of course, also be produced by means of alternation of the positions of the samples 1, 2 while the beams of light remain as of unchanged colours. If the samples 1, 2 are parts of the same face and the face remains immobile, the positions of the samples can be alternated by turning the optics of the apparatus or the entire apparatus over 180°. If this turning is converted to a constant movement of rotation, the detector yields a sine-shaped AC signal if the colour content of the face has a constant gradient within the field of measurement. The phase angle of the signal indicates the sense of the gradient. This feature of the invention is illustrated by FIG. 2. In FIG. 2, the sample areas are designated with reference numerals 1a and 2.

Figure 3:
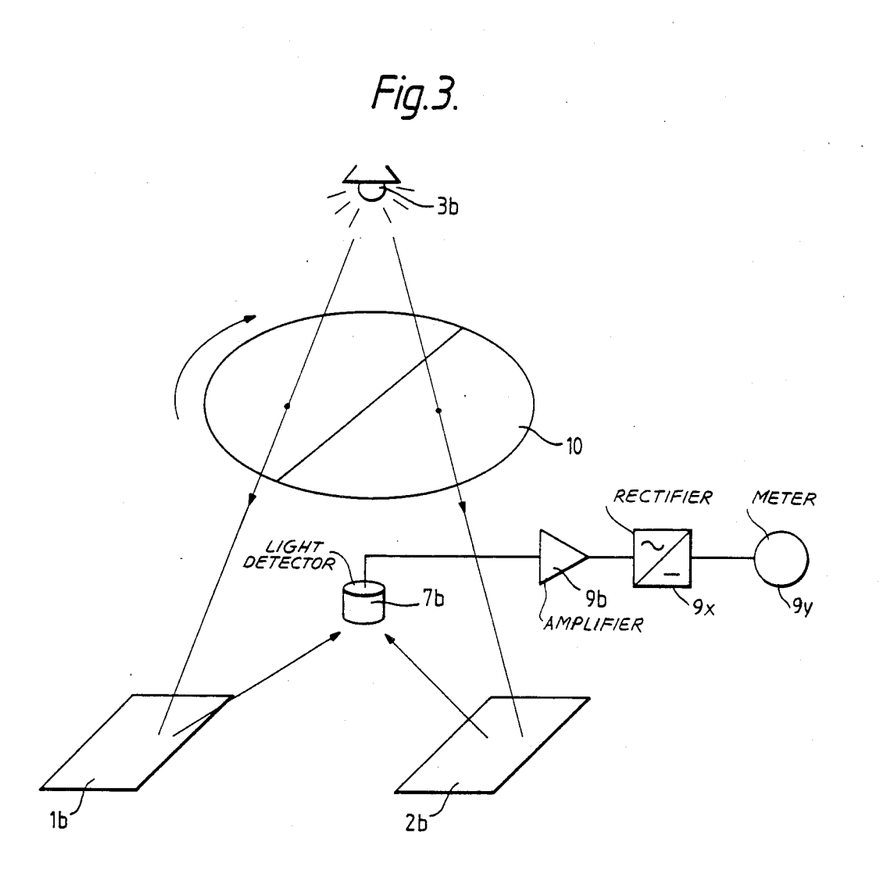
FIG. 3 illustrates an embodiment of the method in which the alternation of the colours is produced by means of a mobile filter.

The method of the instant invention including alteration of spectral ranges as in FIG. 3 is achieved by means of one or several mobile filters. There are two face samples 1b and 2b to be studied. The source of light is a lamp 3b. Between the samples and the lamp, there is a rotary filter 10 consisting of two halves, which are of different colours as compared with each other. The light reflected from the samples 1b and 2b falls on a light detector 7b, whose AC signal is amplified in the amplifier 9b, rectified, by rectifier 9x, and measured by meter 9y.

Figure 4:
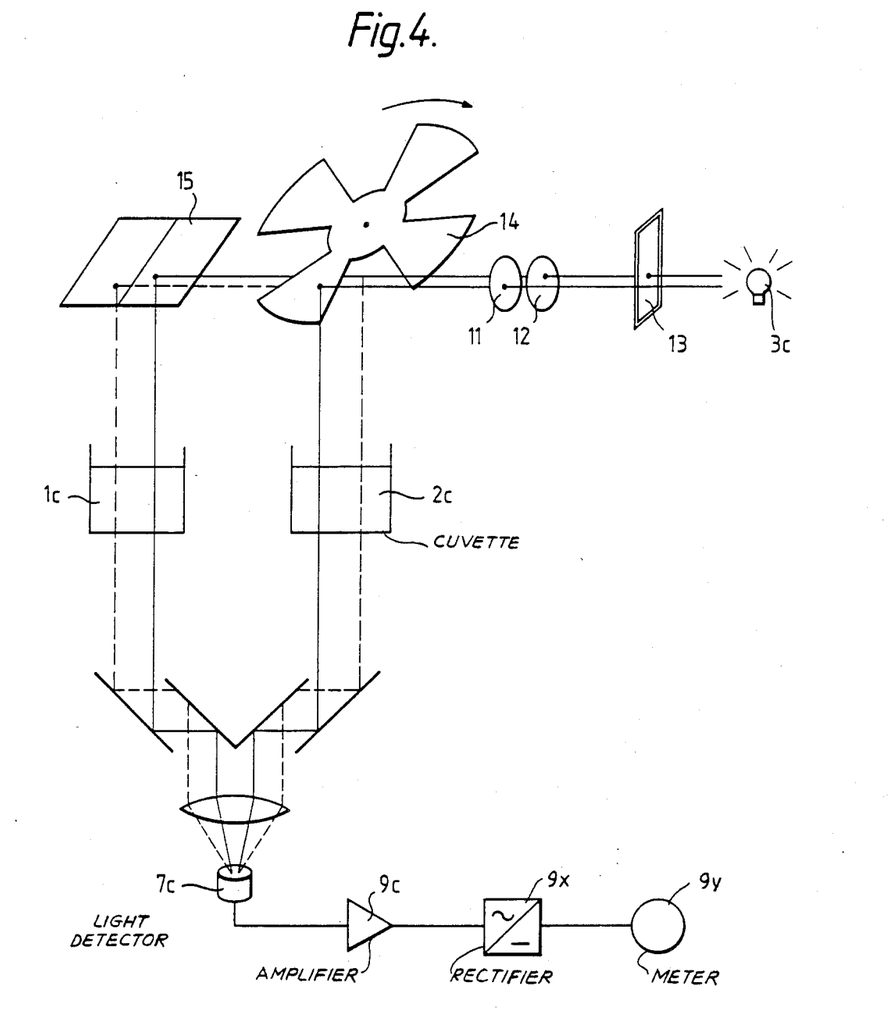
FIG. 4 illustrates an embodiment of the method in which the alternation of the colours is produced by means of a mobile mirror.

The method of the instant invention including the alteration of spectral ranges by means of one or several mobile mirrors is illustrated by FIG. 4. There are two liquid samples to be studied, in cuvettes 1c and 2c. The source of ;ight is the lamp 3c. Of the filters 11 and 12, one is transparent to light of the colour that is absorbed strongly in the colouring agent, and the other one to light that is absorbed weakly in the colouring agent. The filter 13 is a wedge-shaped neutral filter, whose objective is to permit the balance adjustment. The mirror 14 is a rotary breaker mirror, which is placed so in relation to the beams of light that always when one beam of light is reflected by the mirror, the other beam is allowed to pass through an opening. The mirror 15 turns the light passing through an opening of the breaker mirror making it parallel to the light reflected from the breaker mirror. The AC signal of the light deyector 7c is passed to the amplifier 9c, rectified by rectifier 9x, and measured by meter 9y.

Figure 5:
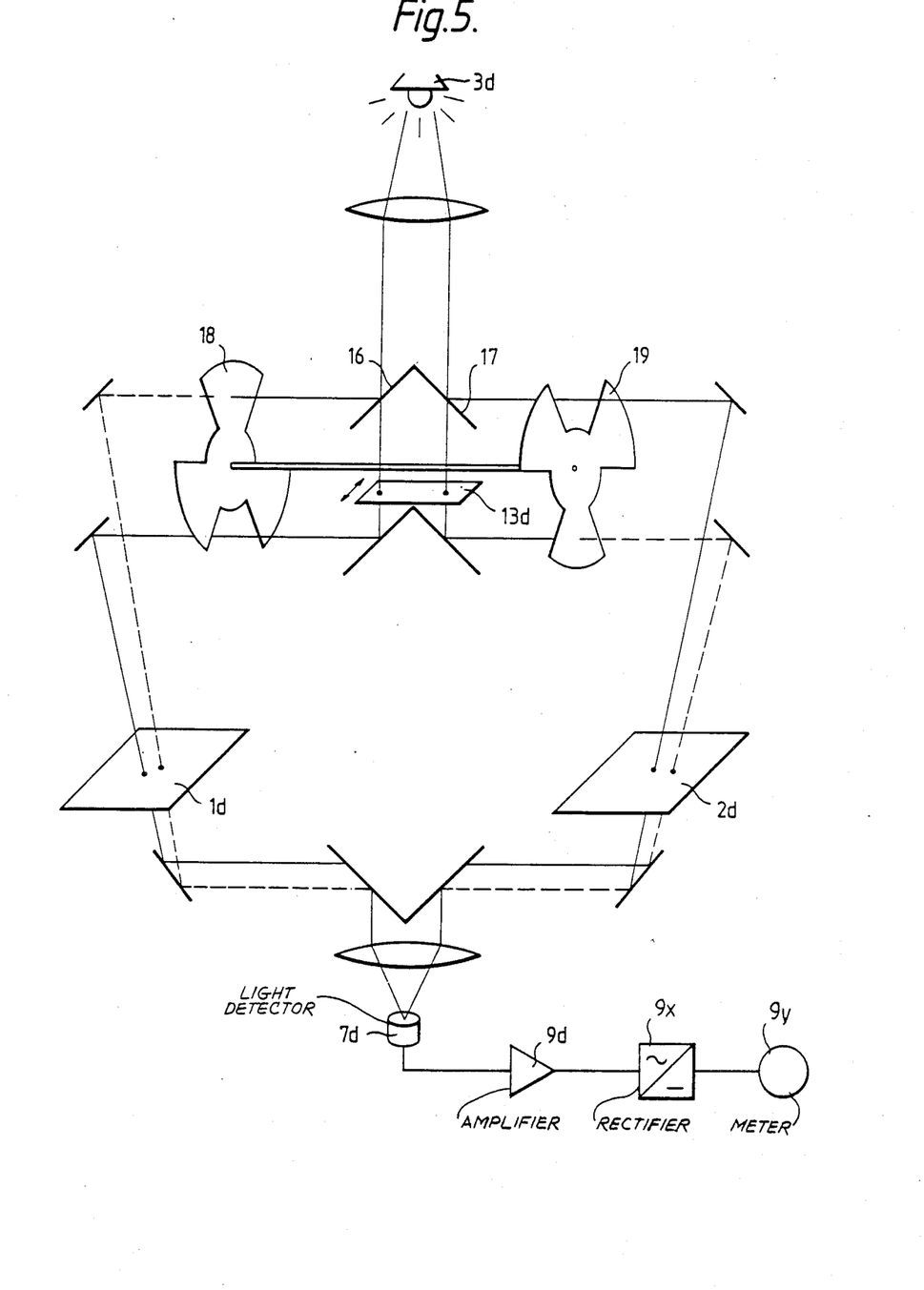
FIG. 5 illustrates an embodiment of the method in which the alternation of the colours is produced by means of light breakers.

The method is of the instant invention including the alternations of spectral ranges by one or several light breakers illustrated by FIG. 5. Therein the apparatus in accordance with the invention is accomplished by means of dichroic filters and two light breakers. The samples are two face samples 1d and 2d. The source of light is a lamp 3d. Two dichroic filters 16 and 17 of the same kind allow a certain wavelength range to pass through and reflect the other wavelengths. A wedge-shaped neutral filter 13d is used for the balance adjustment. The light breakers 18 and 19 are in a fixed position in relation to each other and revolve around the same shaft. Their relative position is such that always when one filter admits light of one colour through it, the other filter admits light of another colour through it. The AC signal of the light detector 7d is passed to the amplifier 9d, rectified by rectifier 9x, and measured by meter 9y.

Figure 6:
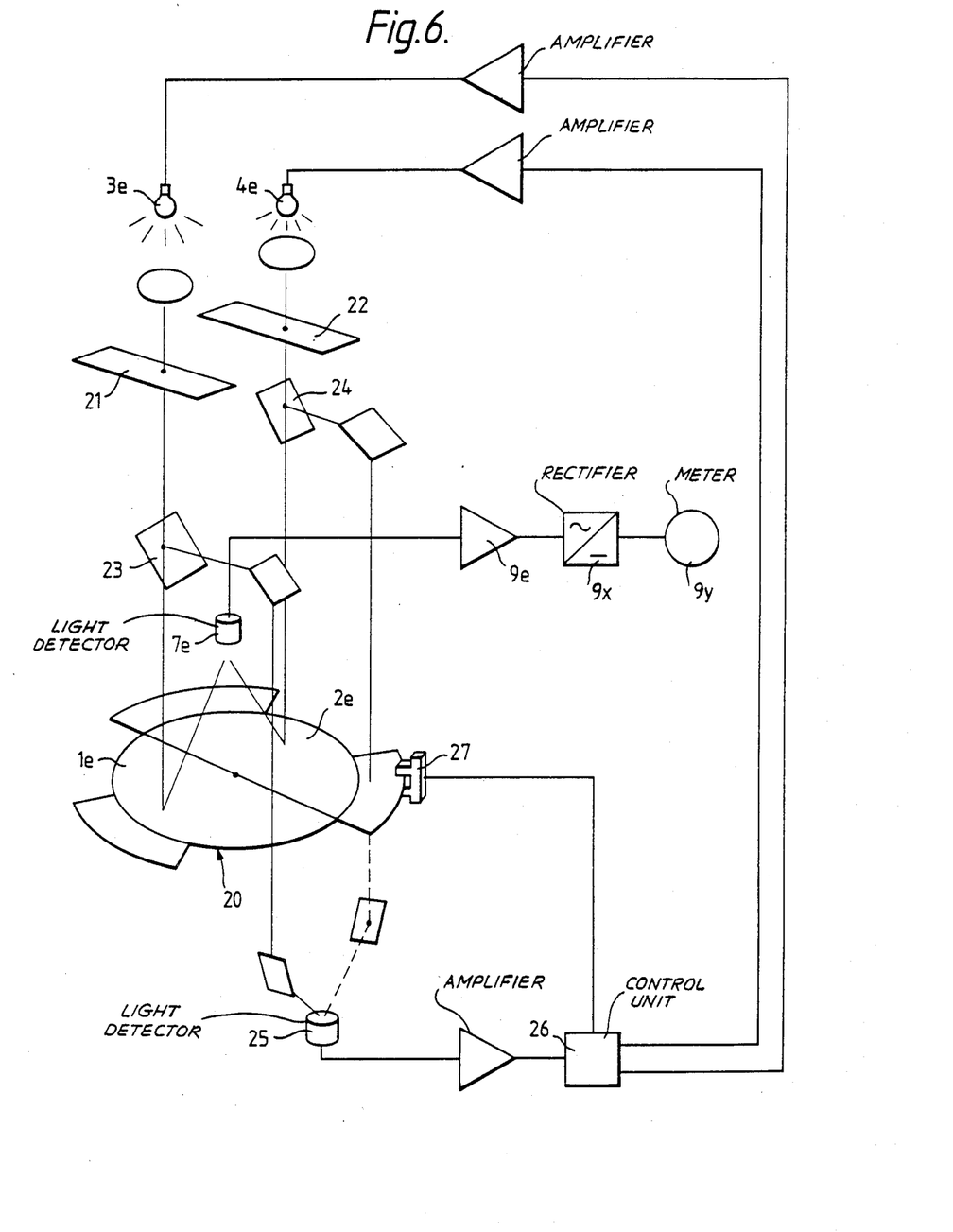

The method of the instant invention including alternating of the spectral ranges by means of a rotating or pendulating movement of the samples, further indcluding a second light detector (25) to which samples are passed alternatingly from both beams of light (3e, 4e) of different spectral ranges at an appropriate frequency, which may be the same as or different from the frequency of alternation of spectral ranges in the measurement, and the AC signal obtained is used for adjusting the ratio of the light intensities of the sources of light (3e, 4e) so that the said AC signal becomes zero, and the DC signal obtained is used for the stabilization of the light intensity of the sources of light (3e, 4e) are illustrated by FIG. 6. The samples are two face samples 1e and 2e, which are attached to a rotary base 20. The source of light consists of two lamps 3e and 4e. The colour of the lights is selected by means of interference filters 21 and 22 of continuous adjustment. These filters admit a narrow wavelength band through them, the average wavelength of the band being selected by shifting the filter in its longitudinal direction in relation to the beam of light. The light reflected from the samples falls on the light detector 7e, whose AC signal is amplified in the amplifier 9e, rectified by rectifier 9x, and measured by meter 9y.

For the stabilization of the sources of light and for automatic balance adjustment, samples are taken from the beams of light after each interference filter by means of beam dividers 23 and 24. The sample beams are passed through a toothing placed at the edge of the rotary base to a light detector 25. The toothing has been dimensioned so that all the time one, and only one, beam of light has access to the detector 25. The spectral sensitivities of the detectors 7e and 25 must be equal. Now, if the detector 25 gives an AC signal, this means that, in view of the spectral sensitivities of the detectors, the light intensities are out of balance. The signal from the detector 25 is fed to the control unit 26, which modifies the brightness ratio of the lamps 3e and 4e so that the AC signal becomes zero. A change in the spectrum of a lamp during adjustment of the brightness is not detrimental, because almost monochromatic light is used in the measurement. For the control, the AC signal of the detector 25 can be rectified, e.g., by means of a phase-sensitive detector; for it, the reference signal is obtained, e.g., from a pair of light transmitter-receivers 27. The DC component of the signal of the detector 25 is proportional to the average value of the intensities of the beams of light. By adjusting the brightness of the lamps 3e and 4e in the same direction, the control unit maintains the DC component of the signal of the detector 25 at a constant value and thereby stabilizes the intensity of light of the lamps.

In general in the invention in accordance with the invention, and in addition to the inclusion of a second light detector (25) to which samples are passed alternatingly from both beams of light (3e, 4e) of different spectral ranges at an appropriate frequency, which may be the same as or different from the frequency of alternation of spectral ranges in the measurement, and the AC signal obtained is used for adjusting the ratio of the light intensities of the soource of light (3e, 4e) so that the AC signal becomes zero, and the DC signal obtained is used for the stabilization of the light intensity of the sources of light (3e, 4e) the DC component of the signal of the measurement detector itself can be taken advantage of in the calibration of the apparatus employing the method. In the case of face samples, if the balance adjustment is performed by means of a black and a white sample, and if the detector is precisely linear, the DC component of the signal of the detector in the balance adjustment is a precise equivalent of the light intensity of one beam of light. If there are two samples in the measurement of which one has no colouring agent at all and the other one is saturated with colouring agent so that it absorbs one of the colours used completely, an AC signal is obtained whose double amplitude is equal to the DC component obtained in the balance adjustment. Thus, when the balance adjustment is being performed, the amplification in the apparatus can be adjusted to such a level that the DC component of the signal of the detector causes, e.g., the reading 100% in the display. If the colouring agent, even when pure, does not absorb any wavelength completely, the calibration must be performed separately by means of a particular calibration sample.

Above, several apparatuses employing the method of the invention have been described, with different embodiments of details corresponding to each other. It is obvious that the scope of protection of the present invention also includes apparatuses in which the said details have been combined in different ways or in which other prior art solutions are used instead of those described above.

What is claimed is:

1. A method for measuring the difference in color content of two samples using an alternating two-step analysis cycle of a frequency from about 1 to 10,000 cycles per second comprising:

arranging a light detector, at least one light source, and at least two sample areas to define a first light path and a second light path;

simultaneously illuminating said first and second sample areas in both steps of said cycle wherein said first sample is illuminated with at least light of a first spectral range in the first analysis step of said analysis cycle and with at least light of a second spectral range distinct from said first spectral range in the second analysis step of the cycle, said second sample area being illuminated with at least light of said second spectral range in said first analysis step of said cycle, and with at least light of said first spectral range in said second analysis step, the first and second sample areas being disposed in the first and second light paths respectively and being composed and arranged to pass light incident therein said light being incident light to the light detector in said first analysis steps detecting by way of said light detector, light of the first spectral range received from the first sample area and from the second spectral range received from the second sample area in said second analysis step detecting by way of said light detector light of said second spectral range received from said first sample area and light of said first spectral range received from said second sample area, said first and second spectral ranges being selected relative to said first and second sample areas such that the difference in the amount of light received at the light detector between the first and second analysis steps is indicative of the difference in color between the sample areas; and generating an AC signal corresponding to the amount of light received by the light detector in the cycle whereby said difference in color between the sample areas may be efficiently determined.

2. Method as claimed in claim 1, further comprising:
(a) said incident light being from light-emitting diodes (3 to 6), and;
(b) alternating the spectral range of said light-emitting diodes by modulating the electric current to said light-emitting diodes.

3. A method as claimed in claim 1 further comprising alternating of the spectral range of said incident light by means of one or several mobile filters (10) mobile between the light source and sample areas with each of said filters being comprised of portions of different colours.

4. Method as claimed in claim 1 further comprising alternating of the spectral range of said incident light within the light path by means of at least one mobile mirror (14) mobile between colour filters and the sample areas such that in a first position the first incident light from a filter is reflected by at least one mirror while the second incident light from another filter does not strike a mirror while in a second position the first incident light from a filter does not strike a mirror while a second incident light from another filter does not strike a mirror.

5. Method as claimed in claim 1 further comprising alternating the incident light by means of at least one light breaker (18, 19), between colour filters and the sample areas alternatingly interrupting incident light such that in a first position the first incident light from a filter to a sample area is blocked but not blocked as to the second area while the second incident light from another filter is blocked as to the second sample area but not as to the first sample area while in a second position the first incident light from a fliter to the first sample area is not blocked but is blockes as to the second sample area, while the second incident light from another filter is not blocked as to the second sample area but is blocked as to the first sample area.

6. Method as claimed in claim 1 further comprising a second light detector (25) and;
(a) alternatingly passing samples of the first incident light and the second incident light (3e, 4e) at an appropriate frequency, which may be the same or different from the frequency of alternating spectral ranges of claim 1 to said second light detector, and;
(b) obtaining an AC signal and;
(c) adjusting the ratio of the light intensities of the sources of light (3e, 4e) so that said AC signal becomes zero, and;
(d) obtaining a DC signal therefrom, and;
(e) stabilizing the light intensity of the sources of light (3e, 4e) by means of said DC signal.

7. The method according to claim 1 wherein light of the first spectral range is weakly absorbed by one sample area and light of the second spectral range is strongly absorbed by the other sample area.

8. The method according to claim 1 wherein light of the first spectral range is strongly absorbed by one of said first and second sample areas and light of said second spectral range is weakly absorbed by the other of said first and second sample areas, and;

simultaneously illuminating said first and second sample areas in both steps of said cycle wherein said first sample area is illuminated with at least light of a first spectral range in a first analysis step of said analysis cycle and with at least light of second spectral range in a second analysis step of the cycle, said second sample area being illuminated with at least light of said second spectral range in said first analysis step and with at least light of said first spectral range in said second analysis step, alternatingly disposing said first and second sample areas in said first and second light path between said at least one light source and said light detector, said first and second sample areas being composed and arranged to pass light incident thereon said light being incident light to the light detector, the light detector means detecting in the first analysis step, light of the first spectral range received from the first sample area and from the second spectral range received from the second sample area and in a second analysis step detecting light of said second spectral range received from said first sample area and light of said first spectral range received from said second area, the first and second spectral ranges being selected respectively relative to said first and second sample areas such that the difference in the amount of light received at the light detector between the first and second analysis steps is indicative of the difference in color between the sample areas; and generating an AC signal corresponding to the amount of light received by the light detector in the cycle whereby said difference in color between the sample areas may be efficiently determined.

9. The method according to claim 8 wherein light of the first spectral range is weakly absorbed by one sample area and the light of the second spectral range is strongly absorbed by the other sample area.

10. Method of claim 8 wherein said sample areas are alternatingly disposed in said light paths by rotating the sample areas.

* * * * *